United States Patent [19]

Dalessandro et al.

[11] Patent Number: 5,338,296
[45] Date of Patent: Aug. 16, 1994

[54] CATHETER AND SHEATH ASSEMBLY

[75] Inventors: David A. Dalessandro, Scotch Plains; George G. Sanderson, Clark; John S. Kula, Budd Lake, all of N.J.

[73] Assignee: Ethicon, Inc., Somerville, N.J.

[21] Appl. No.: 896

[22] Filed: Jan. 6, 1993

[51] Int. Cl.[5] .................................... A61M 29/00
[52] U.S. Cl. ................................. 604/96; 606/194
[58] Field of Search ........................ 604/96–101; 606/192, 194

[56] References Cited

U.S. PATENT DOCUMENTS 4,338,942  7/1982  Fogarty ........................ 604/97

FOREIGN PATENT DOCUMENTS 3326061  2/1984  Fed. Rep. of Germany ........ 604/96

Primary Examiner—Jerome L. Kruter
Attorney, Agent, or Firm—Paul A. Coletti

[57] ABSTRACT

A catheter is provided, adapted to be delivered to a situs in a body passageway by being contained within a sheath. The distal end of the catheter comprises an enlargement which precludes unintended distal motion of the sheath relative to the catheter.

7 Claims, 3 Drawing Sheets

CATHETER AND SHEATH ASSEMBLY

BACKGROUND OF THE INVENTION

This invention generally relates to assemblies for delivering devices to a situs in a body passageway and in particular, to assemblies comprising an outer sheath containing an elongated catheter therein for delivering the distal portion of the catheter to a situs in a body passageway such as a blood vessel or bile duct. The assembly is adapted to be percutaneously inserted into a body passageway, sometimes by means of a guide catheter. For example, the assembly is introduced percutaneously into the femoral artery and then advanced, distally, through the arterial system to a desired situs, e.g. at the situs of an atherosclerotic lesion. Once located, the proximal end of the sheath may be manipulated so as to expose the distal portion of the catheter to the situs, whereafter the intended medical procedure may progress. For example, the so-located distal end of the catheter may include an inflatable balloon for carrying out a percutaneous translumenal coronary angioplasty procedure. Alternatively, a prosthesis such as a stent, graft, or stent/graft combination may be delivered, by the catheter to such situs. The situs need not be in a blood vessel but instead may be some other body passageway such as the urethra or a bile duct. Currently, procedures are performed for stenting such body passageways.

Descriptions of such procedures and the devices and apparatus associated therewith are exemplified by reference to the following U.S. Patents: U.S. Pat. No. 4,299,226 issued Nov. 10, 1981 to Banka; U.S. Pat. No. 4,323,071 issued Apr. 6, 1982 to Simpson, et al.; U.S. Pat. No. 4,581,017 issued Apr. 8, 1986 to Sahota; U.S. Pat. No. 4,748,982 issued Jan. 7, 1988 to Horzewski, et al.; U.S. Pat. No. 4,773,899 issued Sep. 27, 1988 to Spears; U.S. Pat. No. 4,848,344 issued Jul. 18, 1989 to Sos, et al.; U.S. Pat. No. 4,885,003 issued Dec. 5, 1989 to Hillstead; U.S. Pat. No. 4,932,959 issued Jun. 12, 1990 to Horzewski, et al.; U.S. Pat. No. 4,998,917 issued Mar. 12, 1991 to Gaiser, et al.; U.S. Pat. No. 4,998,923 issued Mar. 12, 1991 to Samson, et al.; U.S. Pat. No. 5,007,898 issued Apr. 16, 1991 to Rosenbluth, et al.; U.S. Pat. No. 5,034,001 issued Jul. 23, 1991 to Garrison, et al.; and U.S. Pat. No. 5,116,309 issued May 26, 1992 to Coll.

In carrying out the procedures described and exemplified in using heretofore available apparatus, several difficulties have been encountered and, while in some instances, the art has attempted to cure these difficulties, the state of the art is such that improvement is highly desired.

Specifically, one difficulty heretofore encountered is the problem of threading the elongated catheter through a tortuous passageway system. In doing so, one is faced with the requirement that the assembly have the requisite stiffness (often termed "pushability" in the art) to transmit the pushing forces exerted on the proximal end of the assembly and move the assembly in a distal direction through the passageway without the assembly bending, kinking, crimping or collapsing. At the same time, the assembly must be led through the tortuous passageway, conforming to all the bends and turns that are therein encountered. This need for both stiffness and conformability is in conflict and such conflict heretofore is manifested in disappointing and unsatisfactory performance of prior art devices.

Still another difficulty has been encountered in the employment of the subject devices. In pushing the assemblies through the body passageways, there is the great danger of abrading or otherwise traumatically affecting the inner walls of these passageways. The vascular system is particularly vulnerable to such undesirable abrasion. Still further, generally in connection with an emplaced sheath/contained catheter assembly, there is always the danger that the sheath will move relative to the catheter in an undesired direction, such undesired direction being generally the distal direction. Such movement, for example, during a procedure would obviously be disruptive. Accordingly, there is a need to obviate such undesired movement.

SUMMARY OF THE INVENTION

In accordance with the teachings herein improved catheters and sheaths are provided which can cooperate to form an assembly obviating the above-described shortcomings of prior devices.

In one aspect of this invention a sheath is provided for containing a device to be delivered to a situs in a body passageway e.g., for delivering to such situs the distal portion of a catheter. The sheath comprises an elongated polymeric tube having an open proximal end and an open distal end and a lumen for containing the device, such as a catheter, therein. In accordance with this invention the outside diameter of the sheath at its distal portion is smaller than the outside diameter of such sheath at its proximal portion. Preferably, the smaller diameter distal portion is at only the portion closely adjacent to the distal end and extends for only a small fraction of the length of the sheath at the distal end. Further, the hardness of the polymeric material employed for such smaller diameter portion is less than the hardness of the polymeric material employed for the remainder of the sheath. Finally, the wall thickness of the smaller diameter portion is less than that of the remainder of the sheath. The combination of smaller diameter, lesser hardness and smaller wall thickness results in a flexible, conformable leading distal portion of the assembly as it is being pushed distally through the tortuous body passageway. On the other hand, the major and lagging proximal portion of the sheath by virtue of its larger diameter, harder polymeric material of construction and larger wall thickness, is designed to have the requisite "pushability" to transmit forces and translate the assembly distally through the body passageway. As described herein, all of the above may be accomplished by economically practical manufacturing methods and hence, provides a simple yet highly effective solution to a longstanding problem in this field.

While the differential pushability/conformability of the sheath has been described by a device wherein the diameter, wall thickness and hardness of the respective portions have all been varied, it will be understood that a selection of one or more of these parameters may, in certain instances, produce the desired differential pushability/conformability.

In another aspect of this invention, an elongated catheter is provided having a proximal end and a distal end. The catheter is adapted to be contained in an elongated tubular sheath for the purpose of having the distal end of such catheter delivered to a situs in a body passageway. The catheter comprises an elongated member having at least one lumen therethrough, the member having an outer longitudinally extending surface.

In accordance with the teachings herein, the outer surface is provided with a toroidal enlargement in close proximity to the distal end of the catheter. This toroidal enlargement presents, in the longitudinal cross sectional view of the catheter, a smooth curve. In assembled form, the catheter is contained within the sheath and the inner lumen of the sheath may now be sized such that the distal end of the sheath, in its extreme distal position with respect to the catheter, bears against the proximal portion of the toroidal enlargement and hence is precluded from further distal relocation with respect to the catheter. Accordingly, the highly undesirable relocation of the sheath during a medical procedure is obviated.

The combination of the new sheath as described above together with the catheter taught herein is particularly advantageous in that the reduced diameter of the distal portion of the sheath allows such portion to be impeded distally by the enlargement without increasing the largest profile of the sheath. That is to say, the enlargement may be sized to correspond to the profile of the proximal end of the sheath with the smaller distal end still bearing against the enlargement.

In another aspect of this invention, in the specific case of a catheter carrying a prosthesis such as a stent, the same toroidal enlargement placed distally to the stent will prevent the distal displacement of the stent relative to the catheter.

These and other unique features and benefits of this invention shall be apparent from the following detailed descriptions and drawings.

BRIEF DESCRIPTION OF THE DRAWINGS

The invention will be better understood from the following detailed description of exemplary embodiments thereof taken together with the drawing in which:

FIG. 1 consisting of FIGS. 1A, 1B and 1C, is an elevational, discontinuous view of an assembled sheath and catheter embodying this invention and shown in partial longitudinal cross section wherein

DETAILED DESCRIPTION OF THE INVENTION

Figure 1A:
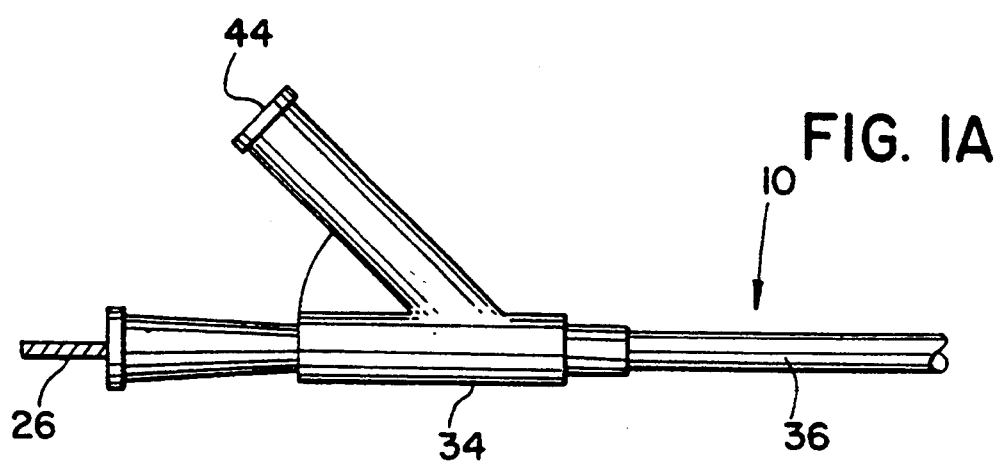
FIG. 1A is the proximal portion of the assembly including a proximal fitting and a guide wire.
Figure 1B:
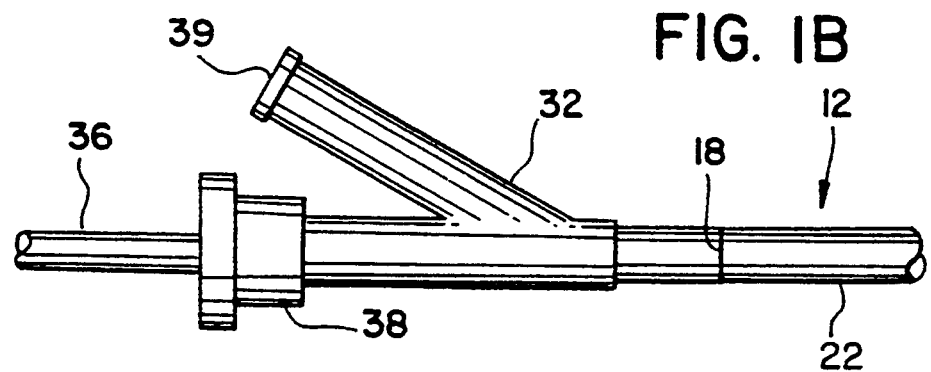
FIG. 1B is an intermediate portion of the assembly including an intermediate fitting.
Figure 1C:
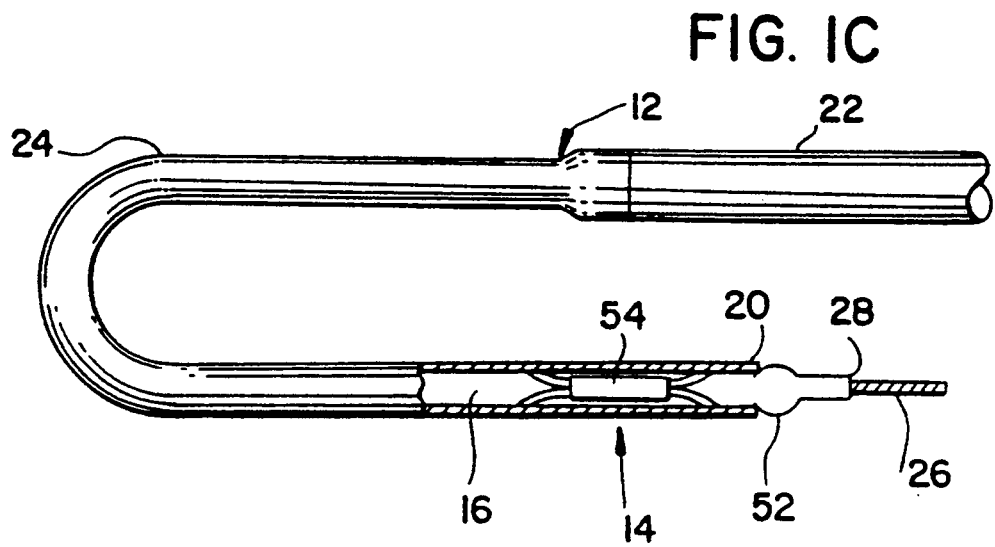
FIG. 1C is the distal portion of the assembly, in partial cross section to reveal an inflatable balloon carrying a stent thereupon.

Referring now to the drawings, illustrated in FIG. 1 (FIGS. 1A thru 1C) is a sheath/catheter assembly 10 embodying the teachings of this invention. The sheath 12 is designed to deliver the distal portion 14 of a device, which in the illustrated embodiment is the balloon catheter 16, to a situs in a body passageway which, for the purpose of this specific exemplification, is a blood vessel such as a coronary artery. It will, of course, be appreciated that other body passageways such as bile ducts or urethras are also contemplated. The sheath 12 comprises an elongated polymeric tube having an open proximal end 18 (hidden in FIG. 1B) and an open distal end 20, and contains the catheter 16 therein. The sheath is divided into a relatively long "pushable" proximal portion 22 and a relatively short conformable distal portion 24. The length of the distal portion 24, in accordance with this invention, is selected to be long enough to conform to the bends and twists of the body passageway through which the assembly must be threaded and lead the remainder of the assembly therethrough. For example, typically a catheter for carrying a stent to a body passageway and passage to the desired situs may range in lengths of from about 35 cm. to about 175 cm. and more typically from about 50 cm. to about 160 cm. The shorter catheters for use in peripheral stenting (e.g., in a femoral or iliac artery) may vary from about 35 cm. to about 90 cm. and the longer catheters for coronary stenting may range from about 90 cm. to about 175 cm. e.g., about 150 cm. The sheath, of course, will be about the same length.

In accordance with the teachings of this invention, it is preferred that the sheath be so divided in distal and proximal portions so that the distal portion is a length of from about 1 cm. to about 35 cm. and more preferably from about 1 cm. to about 12 cm. For example, the distal portion may be 12 cm.

As exemplified, the distal portion 24 of the sheath 12 is more conformable then the relatively stiff proximal portion 22 by virtue of having a relatively smaller diameter, a thinner wall thickness and being constructed of a polymer having a lower hardness value.

The diameter of the distal portion 24 is limited by the highest profile of the contained device in that it is important that such diameter be large enough to allow the distal portion 24 to be easily manipulated to slide over the corresponding distal portion of the device. Beyond this limitation, the diameter should be as small as possible within the practical manufacturing limits so as to present the least trauma and the most conformability to this leading end of the sheath 12. It will be recognized by those skilled in the art that some stiffness will be required but for all practical purposes, a distal portion having the requisite diameter to allow the distal portion of the catheter to slide therein, will have the necessary minimal stiffness to lead the remainder of the sheath through the pathway to the desired situs. In contrast with the distal portion 26, the proximal portion 22 is limited in diameter only by the desire to minimize any trauma to the walls of the body passageways through which it must pass, except of course, it must retain sufficient flexibility to be lead through the pathway by the conformable distal portion. Generally, the constraint with respect to body passageway trauma will control and preclude selecting a diameter for the proximal portion which would be too stiff to manipulate through the pathway. Typically, the distal portion of the sheath may vary from an outside diameter of from about 0.6 mm. (2 French) to about 6 mm. (18 French) and more preferably, from about 0.6 mm. (2 French) to about 2.3 mm. (7 French). The outside diameter of the proximal portion should vary from about 1 mm. (3 French) to about 6.3 mm. (19 French) and more preferably, from about 1 mm. (3 French) to about 2.7 mm. (8 French). For example, the diameter of the distal portion may be 1.55 mm. (4.5 French) and the diameter of the proximal portion may be 1.7 mm. (5 French).

A second contributing factor to the differential pushability/conformability of the distal portion, as compared to the proximal portion, is wall thickness; the distal portion having a wall thickness less than that of the proximal portion. Such wall thickness for the distal portion may vary from about 0.0005 inches to about 0.05 inches and preferably from about 0.001 inches to about 0.006 inches, for example, 0.003 inches. In contrast thereto, the wall thickness of the proximal portion varies from about 0.0006 inches to about 0.06 inches and more preferably, from about 0.004 inches to about 0.006 inches, for example, 0.005 inches.

Still a third factor selected for providing the differential pushability/conformability between the sheath portions is the hardness of the polymer employed; a hard polymer for the pushable proximal portion and a soft polymer for the conformable distal portion. Such polymers as are used currently, generally can be purchased in varying compositions which can result in extruded tubes with varying stiffness. Typically, polymers employed for this purpose are, for example, polyethylenes, polyurethanes, and in some cases, nylons. The polymer of choice is a polyether block polyamide composition sold by the Atochem Corporation of Pennsylvania, under the trade name "PEBAX". Such PEBAX polymer comes in varying hardnesses, ranging from about 25 to about 70 Shore D Durometer values, as the extruded polymer is tested in accordance with the ASTM 1147 standard test procedure for Shore D Durometer values. The proximal portion is preferably about 50 to about 70 in Shore D Durometer and more preferably, about 60 to about 70. In contrast thereto, the distal portion is preferably about 25 to about 60 and more preferably, about 40 to about 60 in Shore D Durometer value.

As best seen in FIG. 1C, the two portions are joined together by force fitting the larger diameter portion into the smaller and then "welding" by the application of energy e.g., heat, whereby the polymers fuse to seal the parts together. In an alternative method of construction the two portions could be continuously co-extruded with polymer of one hardness being first fed to the extruder unit at an upstream station and a polymer of the other hardness being fed in downstream thereof.

Figure 2:
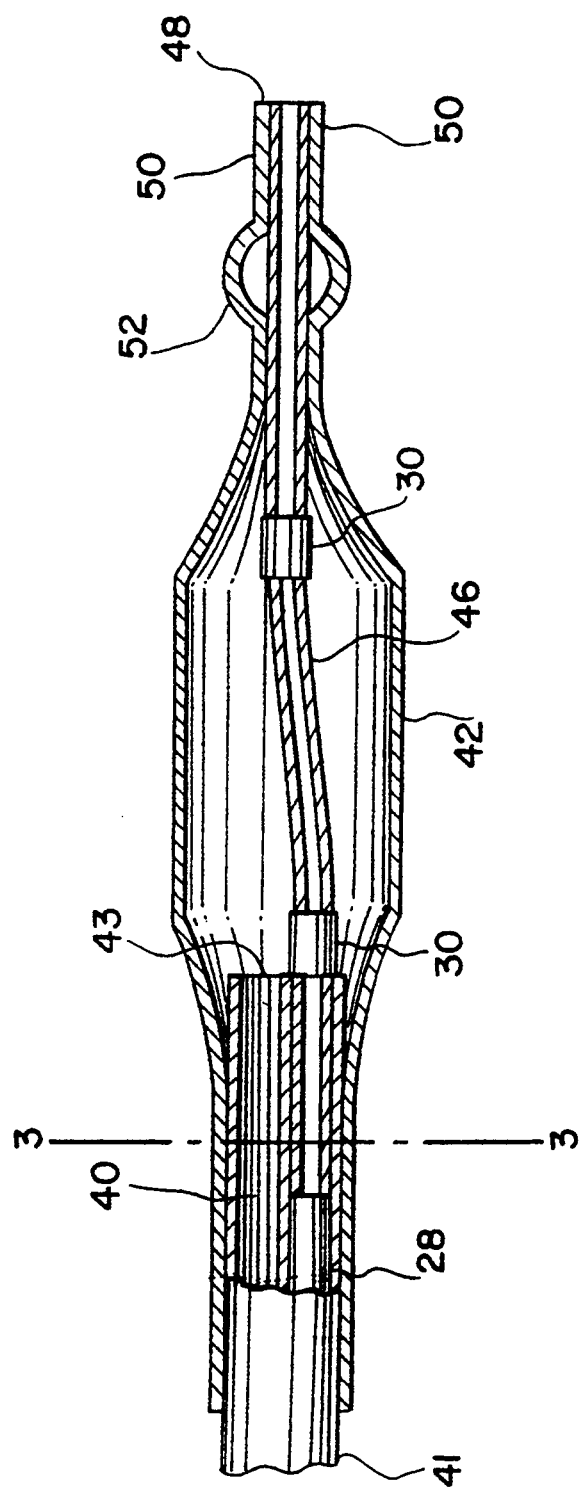
FIG. 2 is an enlarged longitudinal cross sectional view of the balloon catheter embodying the teachings of this invention shown in FIG. 1C, with the sheath removed and the balloon expanded.

Again referring to the drawings, in operation, a guide wire 26 is generally first introduced into the body passageway and then the sheath/catheter assembly 10 is threaded over the guide wire 26 by threading such guide wire through a provided guide wire lumen 28, best viewed in FIG. 2. The annular space between the sheath 12 and the catheter is generally flushed with fluid, such as saline solution, to free the annulus of air which otherwise may be carried into the body passageway. This is accomplished via sheath flush port 39 which is in intermediate fitting 32 and in flow communication with the sheath annulus. The assembly is then advanced through the body passageway until the distal portion of the catheter is in the desired position. Referring to FIG. 2, which illustrates this distal portion of the catheter, radio opaque markers 30 are provided whereby the progress and positioning of the catheter may be monitored by the doctor using x-ray. Once positioned, the distal portion 22 of the sheath may be drawn back proximally to expose the distal portion of the catheter to the situs. This is accomplished by moving the intermediate fitting 32 proximally relative to the proximal fitting 34. The sheath 12 is affixed to this intermediate fitting 32 at its proximal end and the catheter is affixed to the proximal fitting 34 via a stiffening section 36. Accordingly, the translation of the intermediate fitting 32 proximally toward the proximal fitting 34 will result in a proximal withdrawal of the distal portion of the sheath from the catheter. This operation is aided by employing the stiffening section 36 in that the catheter itself is generally flexible and manipulation of the catheter is greatly facilitated by such stiffening means. The sheath may be locked into its position by locking means 38 carried on the intermediate fitting. Such locking means 38 may, for example, comprise a so-called "hemostasis valve e.g., a Tuohy Borst valve".

Figure 3:
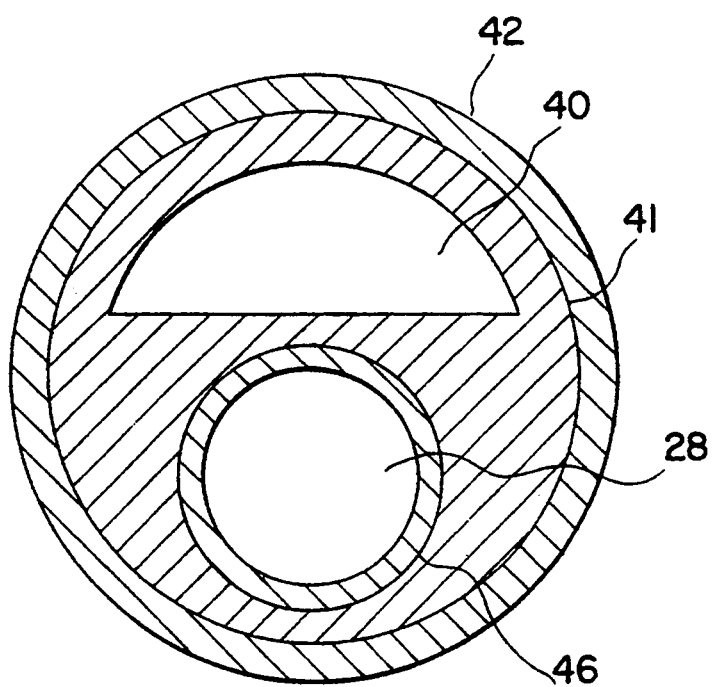
FIG. 3 is an enlarged, transverse cross sectional view of the portion of the catheter illustrated in FIG. 2 and taken through line 3—3.

The catheter itself comprises an elongated tube 41 having an outer surface. As exemplified in the drawings and best seen in FIG. 2 and 3, the elongated tube contains a guide wire lumen 28 and a balloon inflation lumen 40 for carrying fluid to inflate balloon 42. Balloon 42 is circumferentially affixed to the distal end of the elongated tube by such means as welding or gluing. The balloon is made of such a material and is sized such that, in its area of expansion, it is capable of presenting an increased diameter when inflated by pressure exerted by the introduction of inflating fluid directed to the balloon via inflation lumen 40 through inflation lumen port 43. When pressure from such inflation fluid in withdrawn, the balloon collapses to a lesser diameter allowing for the retraction of the catheter. Inflation fluid can be introduced into inflation lumen 40 via inflation fluid port 44 which is contained within proximal fitting 34 and is in flow communication with inflation lumen 40 (see FIG. 1A).

In the embodiment shown in FIG. 2, the wire lumen 28 of the elongated tube 41 terminates at the proximal portion of the balloon. It is necessary for the guide wire 26 to be threaded through the entire catheter and extend from the distal end thereof as is illustrated in FIG. 1C. It is also necessary that the entire lumen carrying the guide wire be sealed so as not be in flow communication with the inflating fluid. These goals are accomplished by inserting into the distal portion of the guide wire lumen 28, a lumen extension 46 which is a lumen containing tube for containing the guide wire in the portion of the catheter extending from the distal portion of the guide wire lumen 28 and through the distal end of the catheter 48. To insure fluid tight sealing, the extension 46 is sealed about the inside surface of the distal portion of the guide wire lumen 28 by adhesive or heat sealing means, for example. At the distal end of the balloon, sealing is provided by extending the balloon into a circumferential flange 50 and sealing this flange 50 to the lumen extension 46. The extension 46 also, usefully, carries the radio-opaque markers 30 which may, for example, be gold bands.

As described herein, heretofore there has been a danger of the undesired movement of the distal end of the sheath with respect to an emplaced catheter. Accordingly, the outer surface of the catheter at the flange 50 of the balloon has been provided with a toroidal enlargement 52 which presents, in the longitudinal cross sectional view shown in FIG. 2, a smooth curved surface. The enlargement is sized relative to the sheath such that when the catheter is contained within the sheath, the distal end 20 of the sheath, in its extreme distal position as shown in FIG. 1C, bears against the enlargement 52 and precludes further distal relocation with respect to the catheter. The curved surface of this enlargement, in addition to precluding such undesired movement of the sheath, has the added benefit of providing a smooth non abrading point of contact with the body passageway as the assembly is being inserted and positioned therein, as contrasted with the blunt end of the sheath, for example. In contrast with the relatively flexible inflatable portion of the balloon which must inflate and collapse, the toroidal enlargement is relatively rigid and remains at all times in its enlarged configuration. This may be accomplished by manufacturing the balloon integrally with the flange 50 carrying the enlargement by a molding process and varying the flexibility of the inflatable section from that of the flange by varying the wall thickness of these sections. As illustrated in the drawings, the wall thickness of the inflatable section of the balloon is shown to be thinner than that of the flange portion. Materials useful for this purpose are such polymers as ethylene-methacrylic acid polymer, polyurethane, polyethyleneterephthalate, with polyethylene being the material of choice. Alternatively, the enlargement may be made of a similar or dissimilar material and attached to the flange by means such as gluing, welding or the like.

As has been described herein and as is illustrated in FIG. 1C, the balloon may carry an expandable stent 54 for emplacement within a body passageway. Such stents and their delivery and function are well described in U.S. Pat. No. 4,733,665 issued Mar. 29, 1988 to Julio C. Palmaz; U.S. Pat. No. 4,739,762 issued Apr. 26, 1988 to Julio C. Palmaz; and U.S. Pat. No. 5,102,417 issued Apr. 7, 1992 to Julio C. Palmaz and Richard Schatz which are all incorporated by reference herein. The toroidal enlargement 52, in connection with the placement of such stents is further useful in precluding the undesirable movement of the stent distally into the body passageway before it is expanded.

While the invention has been described herein in connection with certain preferred embodiments, it will be apparent to those skilled in the art that various modifications and improvements can be made thereto without departing from the scope thereof.

What is claimed:

1. An assembly comprising a sheath for containing a catheter and a catheter contained therein, the distal portion of said catheter to be delivered to a situs in a body passageway, said assembly comprising:
   a sheath comprising an elongated polymeric tube having open proximal and distal ends for containing the catheter therein;
   the diameter of said sheath at its distal portion being smaller than the diameter of said sheath at its proximal portion;
   the hardness of the polymer employed for said distal portion being less than the hardness of said polymer at its proximal portion;
   and the wall thickness of the sheath at its distal portion being less than the wall thickness of the sheath at its proximal portion; whereby said sheath is more flexible at its distal portion then its proximal portion;
   said catheter having a proximal and a distal end and being adapted to be contained within the sheath and comprising:
   an elongated tube having a lumen therethrough and an outer surface;
   said outer surface comprising a toroidal enlargement near the distal end of said catheter, said toroidal enlargement presenting in the longitudinal cross section of the catheter a smooth curve;
   whereby, when said catheter is contained in said sheath, the distal end of said sheath, in its extreme distal position with respect to the catheter, bears against the proximal portion of said enlargement and is precluded from further distal relocation with respect to the catheter.

2. An assembly comprising a sheath for containing a catheter and a catheter contained therein, the distal portion of said catheter to be delivered to a situs in a body passageway, said assembly comprising:
   a sheath comprising an elongated tube having open proximal and distal ends for containing the catheter therein;
   said catheter having a proximal and a distal end and being adapted to be contained within the sheath and comprising:
   an elongated tube having a outer surface and a lumen there through open at the distal end of the catheter for accommodating a guide wire:
   said outer surface comprising a toroidal enlargement near the distal end of the catheter with a hollow center through which said lumen passes;
   said toroidal enlargement presenting in the longitudinal cross section of the catheter a smooth curve; and
   said toroidal enlargement having a surface means which abuts the distal end of said sheath in its extreme distal position with respect to the catheter at the proximal portion of the enlargement to preclude said sheath from further distal relocation with respect to the catheter.

3. The catheter of claim 2 wherein the elongated tube comprises a first elongated tube section having a fixed to its distal end and expandable balloon, said balloon having at its distal end a circumferential flange, said circumferential flange containing said toroidal enlargement.

4. The catheter of claim 3 wherein said balloon is flexible, expandable and collapsible and said flange and its contained enlargement are relatively inflexible and rigid.

5. The catheter of claim 4 wherein said balloon and said flange comprise a single material; said single material being rendered flexible and collapsible in the balloon section by being thin walled and said material being rendered relatively rigid in the flange section by being thick walled.

6. The catheter of claim 5 wherein said balloon and said flange are each selected from materials consisting of surlyn, polyurethane, PET, and polyethylene.

7. The catheter of claim 6 wherein said balloon is selected to be made of polyethylene.

* * * * *